United States Patent [19]

Sasaki et al.

[11] Patent Number: 4,709,071
[45] Date of Patent: Nov. 24, 1987

[54] PROCESS FOR IMPROVING ACTIVITY OF TELLURIUM CONTAINING METAL OXIDE CATALYSTS

[75] Inventors: Yutaka Sasaki; Yutaka Kiyomiya; Toshio Nakamura, all of Kanagawa, Japan

[73] Assignee: Nitto Chemical Industry Co., Ltd., Japan

[21] Appl. No.: 847,074

[22] Filed: May 21, 1986

Related U.S. Application Data

[62] Division of Ser. No. 379,205, May 17, 1982, Pat. No. 4,618,593.

[30] Foreign Application Priority Data

May 15, 1981 [JP] Japan ................................. 56-73144
Feb. 15, 1982 [JP] Japan ................................. 57-21095

[51] Int. Cl.$^4$ .................... C07C 120/14; C07C 120/00
[52] U.S. Cl. ..................................... 558/322; 423/376; 558/316; 558/319; 558/321; 558/327; 558/328
[58] Field of Search .............. 558/322, 329, 319, 316, 558/321, 327, 328; 423/376

[56] References Cited

U.S. PATENT DOCUMENTS

| | | | |
|---|---|---|---|
| 3,164,627 | 1/1965 | Minekawa et al. | 252/461 |
| 3,168,572 | 2/1965 | Voge et al. | 252/439 |
| 3,236,782 | 2/1966 | Koch | 252/411 R |
| 3,882,159 | 5/1975 | Callahan et al. | 260/465.3 |
| 4,330,429 | 5/1982 | Sasaki et al. | 252/413 |
| 4,374,758 | 2/1983 | Sasaki et al. | 252/439 |
| 4,391,880 | 7/1983 | Tsao | 260/465.3 |
| 4,409,122 | 10/1983 | Kleuskens et al. | 502/20 |

FOREIGN PATENT DOCUMENTS

| | | | |
|---|---|---|---|
| 57041 | 8/1982 | European Pat. Off. | 252/411 R |
| 95391 | 3/1978 | Poland . | |
| 963610 | 7/1974 | United Kingdom . | |

Primary Examiner—Joseph Paul Brust
Attorney, Agent, or Firm—Sughrue, Mion, Zinn, Macpeak, and Seas

[57] ABSTRACT

A process for improving the activity of tellurium containing metal oxide catalysts useful as catalysts for oxidation, ammoxidation or oxidative dehydrogenation of organic compounds by heating the catalysts together with a tellurium containing solid and an optional molybdenum containing solid to a temperature up to about 900° C. in a gaseous atmosphere. The process can be effectively applied to deteriorated or spent catalysts, the activity of which has been deteriorated due to use for a long period of time. The tellurium containing solid used as an activity improving agent is elemental tellurium and the molybdenum containing solid is selected from the group consisting of (i) a molybdenum compound, (ii) at least one molybdenum compound supported on an inert carrier, and (iii) a molybdenum enriched catalyst prepared by adding a Mo component to a metal oxide catalyst (which may be a fresh catalyst or a deteriorated catalyst). In a particularly preferred embodiment, the process for improving the activity according to the present invention can be carried out by contacting the deteriorated tellurium containing metal oxide catalyst with the elemental tellurium and optional molybdenum-containing solid in a fluidized-bed. More preferably, the contact is carried out during the oxidation, ammoxidation or oxidative dehydrogenation reaction.

17 Claims, No Drawings

PROCESS FOR IMPROVING ACTIVITY OF TELLURIUM CONTAINING METAL OXIDE CATALYSTS

CROSS REFERENCE TO RELATED APPLICATIONS

This application is a division of application Ser. No. 379,205, filed May 17, 1982, now U.S. Pat. No. 4,618,593.

FIELD OF THE INVENTION

The present invention relates to a process for improving the activity of tellurium containing metal oxide catalysts.

BACKGROUND OF THE INVENTION

Many tellurium containing metal oxide catalysts have been known. For example, it is known that catalysts composed of oxides of molybdenum and tellurium described in U.S. Pat. No. 3,164,626, catalysts composed of oxides of molybdenum, zinc and tellurium described in Japanese Patent Publication 7774/66, catalysts composed of oxides of tellurium and cerium described in U.S. Pat. No. 3,446,834, catalysts composed of oxides of molybdenum, tellurium, manganese and phosphorus described in U.S. Pat. No. 3,335,169, catalysts composed of oxides of iron, antimony, vanadium, molybdenum, tungsten and tellurium described in U.S. Pat. No. 3,668,147, catalysts composed of oxides of molybdenum, tellurium, antimony, cobalt and phosphorus described in Japanese Patent Application (OPI) 141724/79 (the term "OPI" as used herein refers to a published unexamined Japanese patent application), catalysts composed of oxides of tellurium, molybdenum and tungsten, vanadium, chromium, manganese, iron, cobalt, nickel, zinc, tin or bismuth, etc. described in Japanese Patent Publication 16971/80, and catalysts composed of oxides of tin, antimony, copper, iron and tellurium, etc. described in British Pat. No. 1,595,008 are useful for an oxidation, ammoxidation or oxidative dehydrogenation reaction of organic compounds. For example, acrolein (or methacrolein) is formed by an oxidation reaction of propylene (or isobutene) and acrylonitrile (or methacrylonitrile) is formed by an ammoxidation reaction. Further, butadiene is formed by an oxidative dehydrogenation reaction of butene-1 or butene-2.

In the oxidation, ammoxidation or oxidative dehydrogenation reaction of organic compounds, the activity of the catalyst is often observed to deteriorate after use for a long period of time, though the degree thereof varies with the kind of the catalyst or the condition for using it.

Such deterioration of the activity arises from various causes, and a counterplan has been studied from various angles.

Such a phenomenon sometimes occurs in tellurium containing metal oxide catalysts, and the tellurium content in the catalysts sometimes is reduced together with a deterioration of the activity. It is supposed that the catalyst is subjected to irreversible reduction during the reaction and, consequently, tellurium is lost as elemental tellurium, organic tellurium compounds or tellurium hydroxides, etc. which have a comparatively high vapour pressure. However, the cause is not always obvious, because there are many cases that the deterioration of activity is not directly related to the decrease in tellurium content.

Whether the cause is obvious or not, it is important from the viewpoint of practical use to develop catalysts where deterioration occurs with difficulty, to establish a process by which the catalyst is deteriorated with difficulty, and to regenerate the deteriorated catalysts.

Although various processes have been proposed as processes for regenerating deteriorated catalysts, with all of them the processing is carried out after the catalyst is taken out of the reactor. Examples of them include a process for regenerating tellurium containing antimony oxide catalysts described in U.S. Pat. No. 4,049,575, a process for regenerating tellurium containing iron-antimony oxide catalyst described in U.S. Pat. No. 4,208,303 and a process for regenerating tellurium containing antimony compound oxide catalysts described in Japanese Patent Application 67872/80 (EPC Patent Application 0040950), etc.

In regenerating the deteriorated catalyst by these processes, the catalyst must be taken out after the reaction is stopped and, consequently, this causes a large economical loss due to production interruptions.

If the catalytic activity of the catalyst can be restored while the reaction is being carried out or without taking the catalyst out of the reactor even if the reaction is stopped, it would be very advantageous.

As to this, U.S. Pat. No. 3,882,159 discloses a process for regenerating catalysts which comprises contacting in situ a molybdenum containing fluidized-bed catalyst which has become deteriorated during an ammoxidation reaction of propylene with fluidized-bed particles composed of a substantially inactive carrier and molybdenum oxide at the reaction temperature. This U.S. patent is concerned with only regeneration of a molybdenum containing fluidized-bed catalyst, wherein molybdenum oxide supported on an inert carrier is simply used as the regenerating agent. The above described U.S. patent does not disclose a process for improving the activity of tellurium containing metal oxide catalysts.

U.S. Pat. No. 3,236,782 discloses a process for regenerating metal oxide catalysts containing at least Cr, V, Mo or W which comprises contacting the catalyst with a vapour of a compound of the same metal as that present in the catalyst. The process disclosed in this U.S. patent requires a complicated operation in that the catalyst component is introduced as a vapour into the reaction system. Further, this U.S. patent does not disclose a process for improving the activity of tellurium containing metal oxide catalysts.

SUMMARY OF THE INVENTION

An object of the present invention is to solve the above described problems for a tellurium containing metal oxide catalyst, and the present invention is attained by contacting the tellurium containing metal oxide catalyst with a tellurium component in a gaseous phase from a tellurium source.

Accordingly, this invention provides a process for improving the activity of tellurium containing metal oxide catalysts comprising heating the tellurium containing metal oxide catalyst and a tellurium containing solid in a gaseous atmosphere at a temperature up to about 900° C.

In a preferred embodiment, an object of the present invention is to solve the above described problems for tellurium containing metal oxide catalysts, which comprises contacting the tellurium containing metal oxide catalyst with tellurium and molybdenum components in a gaseous phase from a tellurium-molybdenum source during use of the catalyst.

Accordingly, a preferred embodiment of the present invention provides a process for improving the activity of tellurium containing metal oxide catalysts comprising contacting a tellurium containing catalyst used for an oxidation, ammoxidation or oxidative dehydrogenation reaction of organic compounds with both of (a) tellurium or a tellurium compound and (b) a molybdenum compound, during use of the catalyst in the reaction system.

While not desiring to be bound the above described component (a) and component (b) may be present as a tellurium containing solid and a molybdenum containing solid, respectively, or as a tellurium-molybdenum containing solid together. Detailed embodiments of these components (a) and (b) are described hereinafter.

According to the present invention, reduction in the selectivity of the tellurium containing metal oxide catalyst for the desired product and that of the reaction rate due to the passage of time can be prevented simultaneously or improvement in selectivity of the deteriorated catalyst and in the reaction rate can be carried out simultaneously.

The process of the present invention can be very easily applied to a catalyst used for a fluidized-bed reaction. Further, surprisingly the process of the present invention is effective for fresh catalysts. Accordingly, it is clear the process of the present invention is more than merely a process for regenerating catalysts.

Tellurium or a tellurium compound (a) and a molybdeum compound (b) as an optional but suitable component can be easily added to the reaction, if they are solid and have suitable properties, as hereinafter described.

In the fluidized-bed reaction, removal of a portion of the catalyst or adding the catalyst during the reaction can be easily carried out continuously or intermittently. Since these operations are always industrially carried out, the present invention can be practiced in the conventional manner.

The present invention does not result in losses due to production interruptions, because it can be practiced while the reaction is conducted, which is different from many known processes for regenerating catalysts.

When the catalyst and the activity improving agent (the above described component (a) or both of the component (a) and the component (b)) are physically mixed in a dry condition prior to initiation of the reaction and, thereafter, the resulting dry mixture is used for the reaction, an improvement in the activity is similarly observed. Further, when the processing by the present invention is carried out for a catalyst removed from the reactor, the activity is similarly improved. Such a process is also within the scope of the present invention.

Though the mechanism of the present invention is not at presently completely clear, it is supposed that the tellurium component poisons active sites on the catalyst participating in formation of by-products such as carbon dioxide or carbon monoxide, etc. under the reacting condition to control the formation thereof, by which the selectivity for the desired products is improved, and that the molybdenum component, if it is present in the activity improving agent, migrates and deposits on the catalyst to restore the active sites or to produce fresh active sites advantageous for formation of the desired product in cooperation with the tellurium component, by which the reaction rate is increased. In case of using (a) tellurium or a tellurium compound or using component (a) and (b) a molybdeum compound according to the present invention, the time required for exhibiting the effect is generally short. Even in case of using them in a solid condition, the effect can be clearly seen within 1 to 2 hours in many cases. Further, duration of the effect is excellent. Accordingly, migration of the tellurium component from the tellurium containing solid or migration of the tellurium component and the molybdenum component from the tellurium-molybdenum containing solid (or the tellurium containing solid and the molybdenum containing solid) is carried at a comparatively high migration rate. Further, it is believed that the tellurium component or the tellurium and molybdenum components deposited on the catalyst have high affinity to the catalyst components by which the tellurium component or the tellurium and molybdenum components once reacted with the catalyst are not easily separated.

In case of using (a) tellurium or a tellurium compound and (b) a molybdenum compound, in a solid condition, the mechanism of migration thereof to the catalyst is not always clear. In this case, it has been believed that the solid components (a) and (b) move to and deposit on the catalyst in a form which has a comparatively high vapour pressure, such as elemental tellurium, organic tellurium compounds, tellurium hydroxides, organic molybdenum compounds and molybdenum hydroxides, etc. and, particularly, in the case of using the catalyst in a fluidized-bed reaction, there is the possibility that the migration is carried out by physical contact of the activity improving agent with the catalyst.

This mechanism is based on speculation and details thereof are not sufficiently clear, yet. Therefore, means for attaining the object of the present invention which comprises carrying out the reaction while contacting the catalyst with (a) tellurium or a tellurium compound and, if desired, (b) a molybdenum compound should be understood from the above.

DETAILED DESCRIPTION OF THE INVENTION

(A) Tellurium-Containing Metal Oxide Catalyst

It is particularly preferred for the tellurium containing catalysts for the present invention to those used for production of unsaturated aldehydes, unsaturated nitriles, hydrogen cyanide, aromatic aldehydes and aromatic nitriles by an oxidation, ammoxidation or oxidative dehydrogenation reaction of organic compounds.

As the tellurium containing metal oxide catalysts, various kinds of catalysts are known already, as described above.

The process of the present invention can be equally applied to those known tellurium containing metal oxide catalysts and, particularly, it is appropriate for a tellurium containing metal oxide catalyst containing (A) tellurium and (B) at least one element selected from the group consisting of antimony, molybdenum and vanadium.

A preferred catalyst composition is represented by the following empirical formula:

$$A_a Te_b C_c D_d E_e O_x$$

wherein A represents at least one element selected from the group consisting of Sb, Mo, and V, Te represents tellurium, C represents at least one element selected from the group consisting of B, P, As, Bi, S and Se, preferably B, P and Bi, D represents at least one element selected from the group consisting of Li, Na, K, Rb, Cs and Tl, preferably Li, Na, K, Rb, and Cs, E represents at least one member selected from the group consisting of Mg, Ca, Sr, Ba, Y, La, Ce, U, Ti, Zr, Nb, Ta, Cr, W, Mn, Re, Fe, Co, Ni, Ru, Rh, Pd, Os, Ir, Pt, Cu, Ag, Zn, Cd, Al, Ga, In, Ge, Sn and Pb, preferably Mg, Ca, Y, La, Ce, U, Ti, Zr, Nb, Ta, Cr, W, Mn, Fe, Co, Ni, Pd, Cu, Ag, Zn, Cd, Al, Ga, In, Ge, Sn and Pb, and O represents oxygen; and a, b, c, d, e and x each represents the atomic ratio of the elements in the formula for which they are subscripts, wherein for $a=10$, $b=0.01$ to 5 (preferably, 0.05 to 3), $c=0$ to 10 (preferably, 0.005 to 8), $d=0$ to 5 (preferably, 0 to 3), $e=0$ to 60 (preferably, 0.1 to 50) and x is the number of oxygen corresponding to the oxides formed by combining the above described components. The above described tellurium containing metal oxide catalyst in the present invention may be supported on a carrier. For example, silica, silica-alumina, alumina, silica-titania, titania or the like may be employed as the carrier.

The tellurium containing metal oxide catalysts for the present invention preferably have a form for use in a fluidized-bed reaction. Fluidized-bed catalysts preferably have a particle size ranging from about 5 to 200 microns. It is easy to apply the process of the present invention during the fluidized-bed reaction and the effect is great.

Reactions and, particularly, fluidized-bed reactions carried out using such tellurium containing metal oxide catalysts are mainly utilized for production of unsaturated aldehydes, unsaturated acids, unsaturated nitriles, aromatic aldehydes, aromatic nitriles, alkenylbenzenes, heterocyclic aldehydes, heterocyclic nitriles and diolefins by oxidation, ammoxidation and oxidative dehydrogenation reactions of organic compounds.

(B) Tellurium-Containing Solid (Activity Improving Agent)

The tellurium containing solid is the activity improving agent used in the present invention, namely, (a) elemental tellurium or a tellurium compound and, if desired, (b) a molybdenum compound, and various kinds of substances can be used. In preferred embodiments of the present invention, since the catalyst to be processed for improving the activity thereof is that for a fluidized-bed reaction and the processing is carried out while conducting the fluidized-bed reaction, it is preferred for the activity improving agent to be particles capable of being fluidized under the reaction conditions where such is solid. In case of using a finely-divided granular activity improving agent, it is desired for these finely-divided particles to be carefully introduced from a lower portion of the fluidized-bed reactor so as to disperse throughout the catalyst bed.

(1) Kind of Agent and Production Thereof

Examples of the activity improving agent of the present invention include tellurium, hydrogen telluride, tellurium monoxide, tellurium dioxide, tellurium trioxide, tellurous acid, telluric acid and organic tellurium compounds (for example, methanetellurol, ethanetellurol, propanetellurol, butanetellurol, dimethyl telluride, diethyl telluride, dipropyl telluride, dimethyl telluroxide, etc.), tellurium halides, those supported on an inert carrier such as silica, alumina, silica-alumina, titania, silica-titania or zirconia, etc., and tellurium containing metal oxide catalysts enriched with tellurium.

Tellurium metal, hydrogen telluride tellurium dioxide, tellurium trioxide, tellurous acid, telluric acid and organic tellurium compounds, tellurium halides, etc. are commercially available or can be prepared from various tellurium sources using known methods.

In case of using the tellurium component where such is supported on various carriers, various means can be utilized for supporting. For example, tellurium metal, tellurium dioxide, tellurium trioxide, tellurous acid, telluric acid, tellurium nitrate, basic tellurium nitrate, tellurium halide, tellurium sulfate and organic tellurium compounds, etc. can be used as tellurium source, which are mixed with a carrier material such as silica sol, alumina sol or titania sol, etc., followed by spray-drying; or a carrier previously prepared is immersed in or mixed with a solution prepared by dissolving the above described tellurium source. Further, in case of using a tellurium-enriched fluidized-bed catalyst for this purpose, known processes for producing catalysts can be suitably used. Moreover, a catalyst prepared using a known suitable process may be immersed in or mixed with a solution containing the tellurium source directly or after use for the reaction, followed by drying and calcining.

The calcination preferably is conducted at a temperature of from about 200° C. to 900° C. for about 0.5 to 50 hours.

Examples of molybdenum compounds include molybdenum dioxide, molybdenum trioxide, molybdic acid, ammonium paramolybdate, ammonium phosphomolybdate and phosphomolybdic acid, and those supported on an inert carrier as described above, and molybdenum enriched metal oxide catalysts.

Preparations of the molybdenum containing solid can be carried out using the same processes as in the case of preparation of the above described tellurium containing solid.

The tellurium-molybdenum containing solid differs only because the tellurium component and the molybdenum component are present at the same time. Known suitable processes can be used, for example, a process which comprises blending the above described tellurium source and the molybdenum source and molding the resulting mixture, a process which comprises blending both of the above described sources with a carrier component and molding the resulting mixture, and a process for producing fluid catalysts enriched with both of tellurium and molybdenum, etc.

The tellurium containing solid, the molybdenum containing solid and the tellurium-molybdenum containing solid may contain, if desired, other elements in addition to tellurium and/or molybdenum. Namely, they may contain at least one element selected from the group consisting of an alkali metal, an alkaline earth metal, lanthanum, cerium, vanadium, niobium, chromium, tungsten, manganese, iron, cobalt, nickel, copper, zinc, cadmium, titanium, boron, aluminum, gallium, germanium, tin, lead, phosphorus, arsenic, antimony, bismuth, sulfur and selenium. If the activity improving agent is active and the reaction rate is equal to or slightly lower than that of the catalyst when the reaction is carried out in the presence of only the activity improving agent, a positive effect is observed when the amount of addition is not in excess (for example, about 50% or more), even though the selectivity to the desired product is somewhat inferior. In case of using the catalyst enriched with tellurium and molybdenum for the purpose of the present invention, the mixing ratio is not strictly limited, if the reaction rate thereof and selectivity to the desired product are not greatly different from those of the catalyst used.

These various elements such as the above described alkali metals or the like can be used for controlling the migration rate of the tellurium component and/or molybdenum component to the catalyst. Further, these elements can be used for controlling the physical properties of the activity improving agent.

The mixing ratio in the activity improving agent should be selected taking into consideration the above described factors.

(2) Tellurium Content and Molybdenum Content of Agent:

Since it is believed that the tellurium component and the molybdenum component exhibit the effect directly or after conversion into volatile compounds, the effect decreases, if the amounts of the tellurium component and the molybdenum component are too small. Particularly, in case of using tellurium and molybdenum supported on an inert carrier or using a catalyst enriched with these components, these tellurium- and/or molybdenum-containing solids should be sometimes added in a large amount when the tellurium content and/or the molybdenum content thereof is too small.

However, since they are not the catalyst itself for the desired reaction, the catalyst is sometimes diluted by them. Consequently, the volume of the reactor becomes insufficient for sufficiently carrying out the reaction.

Accordingly, it is preferred for the tellurium content in the tellurium containing solid, the molybdenum containing solid or the tellurium-molybdenum containing solid to be about 0.5% by weight or more and preferably about 1.0% by weight or more, and the molybdenum content thereof is about 0.1% by weight or more and preferably 0.5% by weight or more.

It is preferred for the ratio of molybdenum/tellurium (atomic ratio) in the tellurium containing solid and the molybdenum containing solid or the tellurium-molybdenum containing solid to be mixed with the catalyst to be about 0.05:1 to 10:1.

(3) Form of Agent:

In case of using (a) tellurium or a tellurium compound and (b) a molybdenum compound as they are, they may be introduced into the reactor as a powder or they may be physically blended with the catalyst in a dry condition and thereafter added to the reaction system.

In case of using the tellurium component and the molybdenum component as a solid, the properties of these components are important.

In case of a fixed bed reaction, strength is important. Namely, powdering and simultaneous volatilization of the tellurium component or the molybdenum component should be prevented because a pressure drop of the reacting gas in the catalyst bed is increased. In case a fluidized-bed reaction is intended to be used, it is preferred the activity improving agent to be fluidized so as for the agent can be well mixed with the catalyst. Further, in order for the tellurium component and the molybdenum component to be effectively used, the activity improving agent should be present in the reactor for the time necessary to be sufficiently mixed with the catalyst.

Accordingly, in case of use for a fluidized-bed reaction, it is preferred for the particle size of the activity improving agent to be comparatively similar to that of the catalyst and the value of (bulk density of the activity improving agent)/(bulk density of the catalyst) to be in a range of about 0.05:1 to 8:1 and preferably a range of 0.2:1 to 6:1. Further, it is preferred for the fluidized-bed catalyst, in carrying out the present invention, to have a bulk density of about 0.1 to 3 (g/ml) and particle size of about 5 to 200 microns.

(4) Production of Agent by Impregnation Processes:

The kinds of tellurium containing solid as the activity improving agent used in the present invention and the production thereof have been summarized in (1) above. Among the process for production, impregnation processes, particularly, a process for forming a tellurium-enriched or tellurium-molybdenum-enriched solid which comprises impregnating a metal oxide catalyst (fresh catalyst or deteriorated catalyst) with a tellurium component or a tellurium component and a molybdenum component, are particularly advantageous processes for obtaining the activity improving agents of the present invention. The reasons thereof are (1) in the thus resulting activity improving agent, nearly 100% of the tellurium component or the tellurium and molybdenum components added by impregnation rapidly vaporize (within several hours) and they are effectively caught by the tellurium containing metal oxide catalyst to be processed to improve its activity, (2) the activity improving agent from which the tellurium component or the tellurium and molybdenum components added by impregnation are removed by vaporization has properties and activity which are near those of the catalyst to be processed and, consequently, adverse influence upon the reaction after conclusion of its function for improving the activity does not arise, (3) the production is easily carried out because catalysts previously prepared are used, and (4) application to the reaction system is easily carried out and mixing during the reaction is smoothly carried out, because physical properties of the activity improving agent are similar to those of the catalyst used for the reaction (catalyst to be processed).

The production of the activity improving agent by the impregnation process is illustrated in greater detail below.

In case of producing a powder of the tellurium containing solid according to the present invention by impregnating an inert carrier or a metal oxide catalyst with the tellurium component, drying and calcining, a process described in, for example, U.S. Pat. No. 4,049,575, etc. may be used. However, in the present invention, it is not necessary for the tellurium component to form a solid solution with the crystal phase composing the catalyst, in case of, for example, impregnating an antimony type metal oxide catalyst with the tellurium component.

In carrying out impregnation of the carrier (which includes the form of catalyst, hereinafter) with the tellurium component, an impregnating solution containing the tellurium component is preferably carried out using any of the following processes:

(1) Oxidation of tellurium metal by nitric acid,
(2) Dissolution of tellurium dioxide or tellurous acid in nitric acid,
(3) Dissolution of telluric acid in water or nitric acid,
(4) Oxidation of tellurium metal by hydrogen peroxide in the presence of ions and/or a compound selected from the group consisting of
    (a) Ammonium ion
    (b) Alkali metal ion (c) Oxides, oxyacids, salts of oxyacids, heteropolyacids and salts of heteropolyacids of at least one metal selected from the group consisting of vanadium, molybdenum and tungsten, (5) Oxidation of tellurium metal by hydrogen peroxide in the presence of nitric acid, (6) Oxidation by hydrogen peroxide in the presence of iron ion after oxidation of tellurium metal by nitric acid is carried out.

The tellurium containing solid used in the present invention is obtained by impregnating the carrier with the above described solution alone or a mixture of the solution with small amounts of other components, and drying or thereafter calcining. The calcination temperature in this case is from a comparatively low temperature such that moisture is removed to about 900° C. or less, and preferably 850° C. or less.

Preparation of the impregnating solution used for producing the tellurium-molybdenum enriched catalyst, namely, the activity improving agent of the present invention, by impregnating a tellurium containing metal oxide catalyst with a tellurium component and a molybdenum component is preferably carried out using any of the following processes (this impregnating solution can be used, of course, for impregnation of the inert carrier).

(1) At least one member selected from the group consisting of tellurium metal, tellurium monoxide, tellurium dioxide, tellurous acid, tellurium trioxide, and telluric acid and at least one member selected from the group consisting of molybdenum metal, molybdenum dioxide, molybdenum trioxide, ammonium metamolybdate, ammonium paramolybdate, phosphomolybdic acid, silicomolybdic acid, and boromolybdic acid are dissolved in water or nitric acid.

(2) Telluric acid and at least one member selected from the group consisting of oxyacids, salts of oxyacids, heteropoly-acids or salts thereof of molybdenum are dissolved in water or nitric acid.

(3) Tellurium metal is dissolved in hydrogen peroxide in the presence of the oxide, oxyacid, salts of oxyacids, heteropoly-acids, or salts thereof of molybdenum.

In order to produce an impregnating solution having a high concentration, the processes (2) and (3) described above are particularly preferred.

The base catalyst is impregnated with the thus resulting impregnating solution. The base catalyst is a fresh- or a spent or deteriorated fluidized-bed catalyst, which preferably has a particle size of about 5 to 200μ and a pore volume of about 0.1 to 0.8 ml/g. It is preferred for the composition of the base catalyst to be substantially the same as that of the catalyst to be processed in a fresh state, but the compositions may be considerably different from each other. Impregnation is carried out by adding the impregnating solution in an amount of about 0.7 to 1.3 times of pore volume of the base catalyst and mixed with the catalyst. After drying, it is heat-treated at a temperature of from about 200° C. to about 600° C. If desired, impregnation can be carried out several times.

Processing for Improving Activity

The processing for improving the activity of the tellurium containing metal oxide catalyst according to the present invention is carried out by heating the catalyst and the above described tellurium containing solid to a temperature up to about 900° C. in a gaseous atmosphere. It is preferred for the catalyst to be processed and the tellurium containing solid to be in a fluidized state together. In such a case, it is most preferred for the fluidized state of the catalyst to be achieved by carrying out the desired fluidized bed reaction by the catalyst. In such an embodiment, the present invention can be carried out without stopping the fluidized-bed reaction.

The process of the present invention can also be applied to the case where the catalyst to be processed and tellurium containing solid are heat-treated as a fixed bed after physical blending in a dry condition. However, the effect of the present invention is superior in case of carrying out the processing under a fluidized state using the fluidized-bed catalyst. It is believed that the catalyst can greatly move in a fluidized state to result in a large effect.

Suitable gaseous atmospheres for carrying out heating of the catalyst to be processed and the tellurium containing solid (the gas is of course a fluidizing gas when the present invention is carried out under a fluidized state) include inert gases or oxidative gases such as nitrogen, oxygen, carbon dioxide and steam, etc. and gas mixtures of a reducing gas such as organic compounds (for example, methane, ethane, propane, ethene, propylene, propene, butenes, toluene, xylene, methanol, ethanol, isopropanol, etc.), ammonia or carbon monoxide, etc. and oxygen etc.

Although there is the situation where the gas is merely the atmospheric gas for heat-treatment, the gas becomes a reaction atmosphere for the fluidized-bed reaction in case of carrying out activation of the catalyst by the tellurium containing solid during the desired fluidized-bed reaction according to the preferred embodiment of the present invention. For example, a gas mixture composed of organic compounds (for example, methane, ethane, propane, ethene, propylene, propene, butenes, toluene, xylene, methanol, ethanol, isopropanol, etc.), ammonia and oxygen (particularly, air) (and, if desired, steam) is a reaction gas in case of carrying out ammoxidation of a hydrocarbon or an alcohol, and the above described gas mixture from which ammonia is removed is a reaction gas in case of carrying out oxidation or oxidative dehydrogenation.

This gaseous atmosphere should not be excessively reductive. Namely, in case of using reducing gases such as hydrocarbons, ammonia and carbon monoxide, etc., they can not be used alone. If the temperature is increased in the presence of only these reducing gases, the catalyst itself is reduced to result in a deterioration of its activity. It is essential that these reducing gases are used together with oxygen. The term "reducing gas" as used herein means a gas having an ability to reduce the catalyst. Accordingly, the reducing gases described above should be used sometimes as inert gases depending upon the temperature conditions. For example, hydrocarbons and other organic compounds, ammonia and carbon monoxide, etc. can be used as inert gases, in general, at less than about 300° C., because they exhibit poor reducing power to catalysts for such kinds of reactions. In this case, copresence of oxygen is not essential.

Olefins, alcohols and aldehydes are preferably used as the hydrocarbons and other organic compounds. The examples thereof include propene, butenes, toluene, xylene, methanol, ethanol, formaldehyde, acetaldehyde, etc. Saturated hydrocarbons such as methane, propane, butanes, etc. rather are within the category of inert gas to the catalysts for these kinds of reactions.

These reducing gases may be used as a mixture prepared by mixing two or more of the gases in the presence of oxygen or may be used as a mixture prepared by mixing the gases with inert gases.

It is preferred for the tellurium containing solid to be added to the catalyst to be processed in an amount of about 0.01% by weight or more and, preferably, 0.05 to 30% by weight. Within this range, the objects of the present invention can be attained without adversely influencing the activity of the catalyst. When a tellurium containing solid having a high tellurium content is used, the amount theeof may be comparatively small. When a tellurium containing solid having a low tellurium content is used, the amount thereof may be comparatively large. As described above, the tellurium enriched catalyst can be used as a mixture in a suitable ratio when it is used as the tellurium containing solid, provided that it has an abnormal activity.

Activation is carried out at a processing temperature of about 900° C. or less. If it is beyond about 900° C., quality of the catalyst itself changes due to sintering or crystallization, etc. A comparatively high temperature is used in the presence of an inert gas such as nitrogen, oxygen, carbon dioxide or steam, and a comparatively low temperature is used in the presence of a reducing gas such as hydrocarbons and other organic compounds, ammonia or carbon monoxide, etc.

Further, in case that tellurium in the tellurium containing solid is in a state having a comparatively high vapour pressure such as elemental tellurium or organic tellurium compounds, etc. or the tellurium containing solid contains such substances, the processing can be effectively carried out at a low temperature for a short time regardless of the kind of gases. However, in case that such a processing is carried out for the catalyst according to a preferred embodiment of the present invention while conducting the desired fluidized-bed reaction, attention must be paid to the processing temperature, because slightly adverse effects such as reduction of the reaction rate, etc. occur when the processing temperature is too high.

When steam is used as the gaseous atmosphere, attention must be paid to the processing temperature, because the activity of the catalyst sometimes deteriorates due to sintering, if the temperature is higher than about 700° C.

Although the lower limit of the processing temperature can not be determined definitely, it is generally about 200° C. or so.

Since the processing conditions (temperature and time) of the present invention varies according to the tellurium contained solid to be used and the gas to be used, optimum conditions can be easily determined experimentally based on a combination thereof. Further, in case of practicing the present invention while conducting the objective reaction, the conditions used may be the same as those which are conventionally used for an oxidation, ammoxidation or oxidative dehydrogenation reaction of organic compounds.

In a particularly preferred embodiment of the present invention, the activation processing is carried out by contacting the tellurium containing metal oxide catalyst with (a) tellurium or a tellurium compound and (b) a molybdenum compound during conducting an oxidation, ammoxidation or oxidative dehydrogenation reaction of organic compounds. It is preferred for the catalyst to be processed to be contacted with the activity improving agent under fluidized-bed reaction conditions.

As described above, the process of the present invention can be used for fixed-bed reactions by physically blending the catalyst to be processed with the activity improving agent in a dry condition, too. However, the effect of improving the activity is particularly high in case of carrying out the processing while conducting the reaction in a fluidized state using a fluidized-bed catalyst. It is believed that, since movement of the activity improving agent is quick as well as movement of the catalyst, migration of the tellurium component and the molybdenum component to the catalyst is uniformly carried out to result in a good effect.

In case that the activity improving agent is solid, it is preferred for the total amount of the tellurium containing solid and the molybdenum containing solid or the amount of the tellurium-molybdenum containing solid to be about 0.01% to 50% by weight based on the tellurium containing metal oxide catalyst. If the amount thereof is lower than about 0.01% by weight, the effect is very poor and duration of the effect deteriorates in a short time. With respect to the upper limit of the amount, the upper limit is similar to those cases described in the above described section "Kind of the Agent and Production Thereof" for the activity improving agent.

The effect of the activity improving agent is exhibited by migration of the tellurium component and the molybdenum component to the catalyst. Accordingly, from this standpoint, it is preferred for the apparent increment of tellurium content in the catalyst resulting from physically blending the catalyst with the activity improving agent to be about 0.001% to 15% by weight and, preferably, 0.01 to 10% by weight, and the apparent increment of molybdenum therein is about 0.002 to 10% by weight and, preferably, 0.01 to 5% by weight.

The apparent increment of tellurium content and the apparent increment of molybdenum content are defined as follows.

Apparent Increment of Tellurium Content (%) =

$$\frac{\text{Weight of Tellurium in Activity Improving Agent Added (g)}}{\text{Total Weight of Catalyst Packed (g)}} \times 100$$

Apparent Increment of Molybdenum Content (%) =

$$\frac{\text{Weight of Molybdenum in Activity Improving Agent Added (g)}}{\text{Total Weight of Catalyst Packed (g)}} \times 100$$

A preferred amount of the activity improving agent added depends upon the properties of the activity improving agent. In case of a high migration rate of the tellurium component and the molybdenum component, the activity improving agent is sufficient if used in an amount calculated from the desired tellurium and molybdenum contents. In case of a low migration rate of the components, the activity improving agent is preferably used in a slightly larger amount.

The activity improving agent may be physically blended with the catalyst in a dry condition prior to initiation of the reaction or it may be added during the reaction, alone or as a mixture prepared by physically blending the agent with the catalyst in a dry condition. In case of the fluidized-bed reaction, since the catalyst can be safely removed and added while conducting the reaction, no problems in case of using the solid activity improving agent arise.

Addition of the activity improving agent can be carried out several times by observing the conditions of the reaction.

Although it is not necessary to contact the catalyst with the tellurium component together with the molybdenum component, the catalyst may be first contacted with the tellurium component and thereafter contacted with the molybdenum component or the reverse operation thereof may be carried out. However, it is preferable, if possible, to avoid the first addition of only the molybdenum component, because the selectivity for the desired product temporarily decreases by addition of only the molybdenum component at the beginning.

When only elemental tellurium or the tellurium compound is physically blended with the catalyst in a dry condition, the selectivity for the desired product is effectively improved, but the reaction rate hardly varies or sometimes slightly decreases.

On the other hand, when only the molybdenum compound is physically blended with the catalyst in a dry condition, the selectivity for by-products is often increased and, consequently, the selectivity for the desired product often decreases.

As described above, although the addition of the activity improving agent may be carried out using various techniques, it is preferred for the tellurium component and the molybdenum component to be added together.

The condition for carrying out the present invention preferably are the same as that conventionally used for the oxidation, ammoxidation or oxidative dehydrogenation reaction of organic compounds.

Namely, the molar ratio of the feed gas is in a range of about 1:0.3 to 10:0 to 5 as organic compound:oxygen:ammonia (molar ratio), i.e., oxygen:organic compound=0.3:1 to 10:1 and ammonia:organic compound=0:1 to 5:1, and the reaction temperature is in a range of about 300° to 600° C. The reaction pressure used is in a range of atmospheric pressure to about 3 kg/cm$^2$G or so. The feed gas may be used diluted with nitrogen, steam, carbon dioxide, carbon monoxide or helium, etc.

The effects of the present invention are illustrated below by reference to examples and comparative examples.

The yield of the desired product and the selectivity for the desired product are defined herein as follows.

$$\text{Yield (\%)} = \frac{\text{Weight of Carbon in Formed Desired Product}}{\text{Weight of Carbon in Organic Compound Fed as Starting Material}} \times 100$$

$$\text{Selectivity (\%)} = \frac{\text{Weight of Carbon in Formed Desired Product}}{\text{Weight of Carbon in Organic Compound Reacted}} \times 100$$

The Activity Test was conducted as follows.

(1) Ammoxidation Reaction of Propylene

A fluidized-bed reactor having a fluidized catalyst portion of an inner diameter of 5 cm (2 inches) and a height of 2 m was packed with a catalyst in an amount suitably in a range of 1200 g to 1800 g. Into this reactor, a gas having the following composition was introduced to result in an apparent linear velocity of 15 cm/sec. The reaction pressure was atmospheric.

O$_2$ (introduced as air)/Propylene: 2.10 (molar ratio)
NH$_3$/Propylene: 1.15 (molar ratio)

The contact time is defined as follows.

$$\text{Contact Time} = \frac{\text{Volume of Catalyst Packed (l)*}}{\text{Flow Rate of Feed Gas (l/sec)}} \text{ (sec)}$$

*On the bais of apparent bulk density of the catalyst.

(2) Ammoxidation Reaction of Methanol

The same reactor as that used for the above described ammoxidation of propylene was used.

Into this reactor, a gas having the following composition was introduced so as to result in an apparent linear velocity of 15 (cm/sec). The reaction pressure was atmospheric.

O$_2$ (supplied as air)/methanol: 2.10 (molar ratio)
NH$_3$/methanol: 1.20 (molar ratio)
H$_2$O/methanol: 2.00 (molar ratio)
N$_2$/methanol: 5.00 (molar ratio)

The definition of contact time is the same as described above.

(3) Oxidative Dehydrogenation Reaction of Butene

A fixed-bed reactor having an inner diameter of 16 mm and a length of 500 mm was packed with 30 ml of a catalyst. It was heated by a molten salt bath composed of an equivalent mixture by weight of sodium nitrite and potassium nitrate. Into this reactor, a gas having the following composition was introduced in a rate of 7.5 l (NTP) per hour. The reaction pressure was atmospheric.

Air/Butene-1:5 (molar ratio)
Water/Butene-1:1.5 (molar ratio)

Further, unless otherwise indicated, all parts, percents, ratios and the like are by weight.

EXAMPLE 1

A fluidized-bed catalyst having the empirical formula Fe$_{10}$Sb$_{25}$W$_{0.25}$Te$_{1.0}$O$_{67.8}$(SiO$_2$)$_{30}$ was used in an ammoxidation reaction of propylene.

During the reaction, the activity deteriorated due to a reduction of the molar ratio (oxygen/propylene).

Namely, the yield of acrylonitrile fell from 80.3% in the initial stage to 78.6%.

10% of this catalyst was removed and substituted with a tellurium enriched catalyst previously prepared.

Using the resulting mixture of the tellurium containing catalyst and the tellurium containing solid, an ammoxidation reaction of propylene was carried out according to the condition (1) described above to activity test. As a result, the yield of acrylonitrile was improved and it became 80.1% after 3 hours. Thereafter the reaction was continued for 5 hours, but the yield remained at this level.

The tellurium enriched catalyst used in this example was prepared as follows.

2 kg of a fluidized-bed catalyst having the empirical formula Fe$_{10}$Sb$_{25}$W$_{0.25}$Te$_{1.0}$O$_{67.8}$(SiO$_2$)$_{30}$ of the activity of which had deteriorated by use for a long time was removed.

15.1 g of a tellurium metal powder was added to 540 g of 45% nitric acid and dissolved therein. To the resulting solution, 45% nitric acid was added to made 440 ml. The above described deteriorated catalyst was added to the resulting solution and blended well for about 1 hour.

The mixture was calcined at 200° C. for 2 hours and thereafter at 350° C. for 4 hours.

The tellurium content of the resulting tellurium-enriched catalyst was 2.65% by weight.

EXAMPLE 2

A fluidized-bed reactor having an inner diameter of 20 cm (8 inches) was packed with a fluidized-bed catalyst having the empirical formula $Fe_{10}Sb_{25}Cu_{0.5}Mo_{0.25}Te_{1.0}O_{68.3}(SiO_2)_{60}$, and an ammoxidation reaction of propylene was carried out.

Apparent Linear Velocity of Gas Introduced into Reactor: 18 cm/sec
Reaction Pressure: 0.5 kg/cm²G
Molar Ratio or Feed Gas O₂ (suppled as air)/Propylene: 2.2 (molar ratio)
NH₃/Propylene: 1.1 (molar ratio)
Reaction Temperature: 450° C.

When the reaction was carried out for 670 hours under the above described conditions, the acrylonitrile yield decreased and formation of carbon dioxide was increased.

2 kg of the deteriorated catalyst was removed. A tellurium metal powder was added to the deteriorated catalyst in an amount of 0.2%. A fluidized-bed reactor having an inner diameter of 5 cm (2 inches) was packed with the resulting mixture, and fluidization was carried out by introducing nitrogen gas. The temperature was gradually increased and kept at 300° C. for 1 hour.

The thus processed catalyst was utilized for the ammoxidation reaction of propylene. Under condition (1) described above for activity test, though the yield of acrylonitrile of the deteriorated catalyst was 76.3%, that of the processed catalyst was 77.8%.

EXAMPLE 3

2 kg of the deteriorated catalyst in Example 2 was removed.

To the catalyst, 10 g of a tellurium dioxide powder was added. A fluidized-bed reactor having an inner diameter of 5 cm (2 inches) was packed with the resulting mixture, and fluidization was carried out by introducing a 1:1 (by volume) gas mixture of nitrogen and steam. The temperature was gradually increased and kept at 500° C. for 2 hours.

The thus processed catalyst was used for the ammoxidation reaction of propylene under condition (1) described above for activity test.

Although the yield of acrylonitrile of the deteriorated catalyst was 76.3%, that of the processed catalyst was 78.1%.

EXAMPLE 4

2 kg of the deteriorated catalyst in Example 2 was removed.

To the catalyst, 100 g of a powder containing 20% of tellurium dioxide supported on silica was added, and an ammoxidation reaction was carried out according to condition (1) described above for activity test.

Although the yield of acrylonitrile of the deteriorated catalyst was 76.3%, it became 77.5% after 2 hours from initiation of the reaction, and it became 78.3% and 78.2% after 5 hours and 8 hours, respectively.

The powder of tellurium dioxide-silica used in this example was prepared as follows.

160 g of a tellurium metal powder was suspended in 1500 g of water. After adding 10 ml of 15% aqueous ammonia, 400 ml of 35% hydrogen peroxide solution was added little by little to dissolve the tellurium.

To the resulting solution, 2.67 kg of silica sol ($SiO_2$ 30% by weight) was added. After adding 240 g of ammonium nitrate, it was dried by spraying. After calcining at 200° C. for 2 hours and then at 400° C. for 2 hours, it was finally calcined at 550° C. for 4 hours.

When it was analyzed by X-ray diffraction, $TeO_2$ paratellurite was observed.

EXAMPLE 5

The reaction was carried out using the same procedure as in Example 4, except that the mixing ratio of tellurium dioxide to silica powder was 1:2.

The yield of acrylonitrile increased to 77.1% and 77.8% after 5 hours and 8 hours, respectively.

EXAMPLE 6

2 kg of the deteriorated catalyst in Example 2 was removed.

To the catalyst, 100 g of a powder wherein oxides of tellurium and molybdenum were supported on silica-alumina was added, and the mixture was processed at 400° C. for 3 hours by introducing a gas mixture of ammonia and the air (ammonia content 9% by volume).

Then, an ammoxidation reaction of propylene was carried out according to condition (1) described above for activity test. The yield of acrylonitrile increased to 78.4%.

The powder containing oxides of tellurium and molybdenum used in this example was prepared as follows.

920 g of a fluidized-bed catalyst carrier composed of silica-alumina was removed.

64 g of a tellurium metal powder was suspended in 300 ml of water containing 9 g of ammonium paramolybdate and the suspension was heated to about 95° C. 170 ml of 35% hydrogen peroxide solution was added little by little to dissolve the tellurium completely. After the quantity of liquid was adjusted with pure water to make 580 ml, the above described silica-alumina catalyst carrier was added thereto and blended for 1 hour with a blender.

Then, the mixture was dried at 130° C. for 3 hours and calcined at 400° C. for 2 hours and at 500° C. for 2 hours.

EXAMPLE 7

Using a catalyst having the empirical formula $Fe_{10}Sb_{25}Cu_3Mo_{0.5}W_{0.3}Te_{1.5}O_{73.4}(SiO_2)_{60}$, an ammoxidation reaction of propylene was carried out.

Since the molar ratio of oxygen/propylene was allowed to decrease during the reaction, the catalyst deteriorated. As the result, the yield of acrylonitrile was 83.2% even though the condition was returned to the standard condition.

To this catalyst, a tellurium-molybdenum enriched catalyst was added in a mixing ratio of 7%, and the reaction was carried out according to condition (1) described above for activity test. The yield of acrylonitrile gradually increased to become 85.0% after the reaction was carried out for 3 hours.

The tellurium-molybdenum enriched catalyst used in this example was prepared as follows.

1.5 kg of the deteriorated catalyst formed in Example 2 was removed.

13.5 g of a tellurium metal powder was added little by little to 45% nitric acid and dissolved therein.

3.75 g of ammonium paramolybdate was dissolved in 10 ml of pure water, and the resulting solution was added to the above described solution of tellurium nitrate. After the quantity of liquid was adjusted by adding pure water to make 420 ml, the deteriorated catalyst was added and well blended for 1 hour with a blender.

After heat treatment at 200° C. for 5 hours and at 400° C. for 2 hours, it was calcined at 550° C. for 4 hours.

EXAMPLE 8

Using the same catalyst as in Example 7, the following procedure was carried out.

Since the molar ratio of oxygen/propylene was allowed to decrease during the reaction, the catalyst deteriorated. As the result, the yield of acrylonitrile became 82.8% even though the condition was returned to the standard condition.

To this catalyst, the same tellurium-molybdenum enriched catalyst as that in Example 7 was added in an amount of 3%, and the reaction was carried out again. The yield of acrylonitrile gradually increased to become 84.8% after the reaction was carried out for 5 hours.

EXAMPLE 9

To the same catalyst as that in Example 7, a tellurium dioxide-silica powder prepared in Example 4 was added in an amount of 2%, and an ammoxidation reaction of propylene was carried out according to condition (1) for activity test.

The yield of acrylonitrile increased by 0.6%, but formation of carbon dioxide and hydrogen cyanide slightly decreased.

In this example, a fresh catalyst (which was not deteriorated) was processed according to the present invention. Due to this processing, the selectivity for acrylonitrile was improved, and the processed catalyst showed activity superior to the fresh catalyst (which was not deteriorated).

COMPARATIVE EXAMPLE 1

To the same type of catalyst as that in Example 7, a tellurium dioxide-silica powder prepared as in Example 4 was added in an amount of 2%, and fluidization as carried out by passing a mixed gas composed of nitrogen and ammonia (ammonia 10% by volume) and processed at 450° C. for 20 minutes.

Then, activity by an ammoxidation reaction was examined. However, the reaction could not be continued, because a normal reaction could not be carried out because of the large amount of carbon dioxide generated.

In carrying out the processing with a reducing gas (+ inert gas) in the absence of oxygen, it is obvious that the activity was markedly deteriorated instead of improved.

EXAMPLE 10

A fluidized-bed catalyst having the empirical formula $Te_{0.5}Mo_{10}W_1Fe_2Co_3Ni_2Bi_1K_{0.1}O_{43.6}(SiO_2)_{50}$ was utilized for an ammoxidation reaction of methanol under condition (2) above for activity test.

When the reaction was carried out along with reducing the molar ratio of a feed gas (oxygen/methanol), the yield of hydrogen cyanide gradually reduced. Although the molar ratio was returned to the standard condition for the activity test, the yield of hydrogen cyanide which was 84.1% in the initial stage fell to 82.6%.

To this deteriorated catalyst, a tellurium dioxide-silica powder prepared as in Example 4 was added in an amount o 5%, and the reaction was carried out again. The yield of hydrogen cyanide increased with the passage of time to become 83.9% after 3 hours.

EXAMPLE 11

300 g of a fluidized-bed catalyst having the empirical formula $Fe_{10}Sb_{25}W_{0.25}Te_{1.0}O_{67.8}(SiO_2)_{30}$ (that described in Example 1) was removed and kneaded with added water. It was molded in a cylindrical form of 2 mm×2 mm φ and dried.

Using this catalyst, an oxidative dehydrogenation reaction of butene-1 was carried out under condition (3) for activity test.

At a reaction temperature of 370° C., the conversion of butene-1 was 94% and the yield of butadiene was 82%. When the reaction was carried out by increasing the reaction temperature to 380° C., formation of carbon dioxide increased and excess oxygen became zero. Therefore, the reaction was stopped. Although the temperature was reduced to conduct the reaction again at 370° C., the conversion of butene-1 was 91% and the yield of butadiene was 78%.

This deteriorated catalyst was removed. Tellurium dioxide-silica pellets previously prepared (which were prepared by molding the powder as described in Example 4 by the same method as that for the above described catalyst) were added in an amount of 5% to the catalyst, and the reaction was carried out again.

Three hours after the initiation of the reaction, the conversion of butene-1 became 92% and the yield of butadiene became 80%.

The summary of conditions and results of Examples 1 to 10 and Comparative Example 1 above described are shown in Table 1 below.

TABLE I

| | Properties and Mixing Condition of Tellurium-Containing Solid | | | | | Results of Activity Test | | | |
|---|---|---|---|---|---|---|---|---|---|
| | Bulk Density (g/ml) | Te Content (% by weight) | Surface Concentration of Te (atomic %) | Ratio of Bulk Density of Catalyst | Mixing Ratio to Catalyst (%) | Reaction Temperature (°C.) | Contact Time (sec) | (%) | (%) |
| | | | | | | | | Yield of Acrylonitrile | Total Conversion of Propylene |
| Example 1 | | | | | | | | | |
| (A) Before deterioration | — | — | — | — | — | 460 | 6.0 | 80.3 | 98.6 |
| (B) After deterioration | 0.83 | — | — | — | — | 460 | 6.0 | 78.6 | 97.5 |
| Tellurium enriched catalyst | 0.84 | 2.65 | 0.52 | 1.01 | 11.1 | 460 | 6.0 | 77.3 | 95.2 |
| (C) After activation processing | (processing gas: propylene, ammonia, oxygen and nitrogen) | | | | — | 460 | 6.0 | 80.1 | 97.8 |
| Example 2 | | | | | | | | | |

TABLE I-continued

| | | Properties and Mixing Condition of Tellurium-Containing Solid | | | | Results of Activity Test | | | |
|---|---|---|---|---|---|---|---|---|---|
| | | Bulk Density (g/ml) | Te Content (% by weight) | Surface Concentration of Te (atomic %) | Ratio of Bulk Density of Catalyst | Mixing Ratio to Catalyst (%) | Reaction Temperature (°C.) | Contact Time (sec) | (%) | (%) |
| (A) Before deterioration | | — | — | — | — | — | 460 | 3.5 | 78.0 | 98.3 |
| (B) After deterioration | | 0.90 | — | — | — | — | 460 | 4.0 | 76.3 | 97.8 |
| | Tellurium metal powder | 2.14 | 93.2 | 78.3 | 2.38 | 0.2 | — | — | — | — |
| (C) After activation processing | | (processing gas: nitrogen) | | | | — | 460 | 4.0 | 77.8 | 98.0 |
| Example 3 | | Catalyst as described in Example 2 | | | | | | | | |
| (B) After deterioration | | 0.90 | — | — | — | — | 460 | 4.0 | 76.3 | 97.8 |
| | Tellurium dioxide powder | 1.40 | 77.6 | 22.2 | 1.56 | 0.5 | — | — | — | — |
| (C) After activation processing | | (processing gas: nitrogen and steam) | | | | — | 460 | 4.0 | 78.1 | 97.9 |
| Example 4 | | Catalyst as described in Example 2 | | | | | | | | |
| (B) After deterioration | | 0.90 | — | — | — | — | 460 | 4.0 | 76.3 | 97.8 |
| | Tellurium dioxide-silica powder | 0.98 | 16.0 | 1.9 | 1.09 | 5.0 | — | — | — | — |
| (C) After activation processing | | (processing gas: propylene, ammonia, oxygen and nitrogen) | | | | — | 460 | 4.0 | 78.3 | 98.0 |
| Example 5 | | Catalyst as described in Example 2 | | | | | | | | |
| (B) After deterioration | | 0.90 | — | — | — | — | 460 | 4.0 | 76.3 | 97.8 |
| | Tellurium dioxide-silica powder | As described in Example 4 | | | 1.09 | 2.5 | — | — | — | — |
| (C) After activation processing | | (processing gas: propylene, ammonia, oxygen and nitrogen) | | | | — | 460 | 4.0 | 77.8 | 97.6 |
| Example 6 | | Catalyst as described in Example 2 | | | | | | | | |
| (B) After deterioration | | 0.90 | — | — | — | — | 460 | 4.0 | 76.3 | 97.8 |
| | Te—Mo—silica-alumina | 0.51 | 6.4 | 2.1 | 0.57 | 5.0 | — | — | — | — |
| (C) After activation processing | | (processing gas: ammonia, oxygen and nitrogen) | | | | — | 460 | 4.0 | 78.4 | 98.1 |
| Example 7 | | | | | | | | | | |
| (A) Before deterioration | | — | — | — | — | — | 450 | 3.0 | 85.1 | 98.2 |
| (B) After deterioration | | 0.90 | — | — | — | — | 450 | 3.0 | 83.2 | 96.8 |
| | Tellurium-molybdenum enriched catalyst | 0.91 | 2.37 | 1.6 | 1.01 | 7.0 | 450 | 3.0 | 78.6 | 97.0 |
| (C) After activation processing | | (processing gas: propylene, ammonia, oxygen and nitrogen) | | | | — | 450 | 3.0 | 85.0 | 97.3 |
| Example 8 | | Catalyst as described in Example 7 | | | | | | | | |
| (B) After deterioration | | 0.90 | — | — | — | — | 450 | 3.0 | 82.8 | 96.1 |
| | Tellurium-molybdenum enriched catalyst | As described in Example 7 | | | 1.01 | 3.0 | 450 | 3.0 | 78.6 | 97.0 |
| (C) After activation processing | | (processing gas: propylene, ammonia, oxygen and nitrogen) | | | | — | 450 | 3.0 | 84.8 | 96.5 |
| Example 9 | | Catalyst as described in Example 7 | | | | | | | | |
| (A) Before processing | | 0.90 | — | — | — | — | 450 | 3.0 | 85.1 | 98.2 |
| | Tellurium dioxide-silica powder | As described in Example 4 | | | 0.57 | 2.0 | — | — | — | — |
| (C) After activation processing | | (processing gas: propylene, ammonia, oxygen and nitrogen) | | | | — | 450 | 3.0 | 85.7 | 98.4 |
| Comparative Example 1 | | Catalyst as described in Example 7 | | | | | | | | |
| (A) Before processing | | 0.90 | — | — | — | — | 450 | 3.0 | 85.1 | 98.2 |
| | Tellurium dioxide-silica powder | As described in Example 4 | | | 0.57 | 2.0 | — | — | — | — |
| (C) After activation processing | | (processing gas: ammonia and nitrogen) | | | | — | 450 | 3.0 | Since a large amount of CO$_2$ is formed, normal reaction can not be carried out. | |
| | | | | | | | | | Yield of Hydrogen Cyanide | Total Conversion of Methanol |
| Example 10 | | | | | | | | | | |
| (A) Before deterioration | | — | — | — | — | — | 430 | 2.0 | 84.1 | 96.2 |
| (B) After deterioration | | 0.95 | — | — | — | — | 430 | 2.0 | 82.6 | 94.9 |
| | Tellurium dioxide-silica powder | As described in Example 4 | | | 0.54 | 5.0 | — | — | — | — |
| (C) After activation processing | | (processing gas: methanol, ammonia, oxygen and nitrogen) | | | | — | 430 | 2.0 | 83.9 | 95.1 |

The surface concentration of tellurium in Table 1 was measured by XPS (X-ray photoelectron spectroscopy), which are indicated as atomic % of detected element.

The measurement was carried out by means of PHI 550 type apparatus, and the sample was supported on a copper tape.

In using catalysts enriched with tellurium (or tellurium-molybdenum) as the tellurium containing solid, the results of activity test of themselves are shown in the table together. In every cases, the yield of acrylonitrile was lower and the reaction rate was smaller than those in case of using the catalyst.

It is unexpected that the results of the reaction are improved instead of deteriorated, in case of carrying out the reaction by adding such a tellurium (or tellurium-molybdenum) enriched catalyst, as compared with the case of using the base catalyst alone.

In case that tellurium, tellurium dioxide or another tellurium compound is used as supported on a carrier, the activity thereof for the desired reaction is further low.

EXAMPLE 12

A fluidized-bed catalyst having the empirical formula $Fe_{10}Sb_{25}W_{0.25}Te_{1.0}O_{67.8}(SiO_2)_{30}$ was used for an ammoxidation reaction of propylene under condition (1) for activity test.

The activity was deteriorated by reduction of the molar ratio (oxygen/propylene) during the reaction.

Namely, the yield of acrylonitrile which was 80.3% initially became 76.1%.

When the reaction was continued for mixing 1.0% of a tellurium-molybdenum containing solid containing 38.3% of tellurium, 2.9% of molybdenum and 47.8% of silicon dioxide with the catalyst, the yield of acrylonitrile became 80.5% after 2 hours. Thereafter the reaction was continued for 3 hours, but the yield of acrylonitrile did not change.

EXAMPLE 13

A fluidized-bed reactor having an inner diameter of 20 cm was packed with a fluidized-bed catalyst having the empirical formula $Fe_{10}Sb_{25}Cu_3Mo_{0.5}W_{0.3}Te_{1.5}O_{73.4}(SiO_2)_{60}$, and an ammoxidation reaction of propylene was carried out.

| Apparent Linear Velocity of Gas Introduced into Reactor | 18 cm/sec |
|---|---|
| Reaction Pressure | 0.5 kg/cm² G |
| Molar Ratio of Feed Gas | |
| Air/Propylene | 10.5 (molar ratio) |
| Ammonia/Propylene | 1.05 (molar ratio) |
| Reaction Temperature | 450° C. |

When the reaction was carried out for 500 hours under the above described conditions, the yield of acrylonitrile deteriorated.

When this deteriorated catalyst was removed and subjected to activity test under condition (1) for activity test, the yield of acrylonitrile was 83.0%.

To this catalyst, a tellurium-molybdenum containing solid containing 35.2% of tellurium, 7.9% of molybdenum and 44.0% of silicon dioxide was added in an amount of 1.1% based on the catalyst while conducting the reaction. Two hours after the addition of the tellurium-molybdenum containing solid, the yield of acrylonitrile became 85.5%.

EXAMPLE 14

To a deteriorated catalyst as in Example 13, the same tellurium-molybdenum containing solid as that described in Example 13 was added in an amount of 1.7% based on the catalyst, and an ammoxidation reaction of propylene was carried out under condition (1) for activity test.

Two hours after the initiation of the reaction, the yield of acrylonitrile became 85.3%.

EXAMPLE 15

A fluidized-bed catalyst having the empirical formula $Te_{0.5}Mo_{10}W_1Fe_2Co_3Ni_2Bi_1K_{0.1}O_{43.6}(SiO_2)_{50}$ was used for an ammoxidation reaction of methanol according to condition (2) for activity test.

By carrying out the reaction with a low molar ratio (oxygen/methanol) of the feed gas, the yield of hydrogen cyanide gradually deteriorated. Although the molar ratio was returned to the standard condition for activity test, the yield of hydrogen cyanide which was 84.1% initially deteriorated to become 82.0%.

Thus, a tellurium containing solid containing 20.0% of tellurium (which was composed of silicon and oxygen in addition to tellurium) was added in an amount of 1.3% based on the catalyst and a molybdenum containing solid containing 66.7% of molybdenum (which was composed of oxygen in addition to molybdenum) was added in an amount of 0.15% based on the catalyst.

The yield of hydrogen cyanide and the total conversion of methanol were improved with the passage of time. After 1 hour, the yield of hydrogen cyanide became 84.3% and the total conversion of methanol became 96.5%.

EXAMPLE 16

300 g of a fluidized-bed catalyst having the empirical formula $Fe_{10}Sb_{25}W_{0.25}Te_{1.0}O_{67.8}(SiO_2)_{30}$ (which was the same as described in Example 12) was removed and kneaded with adder water. It was molded in columns of 2 mm × 2 mm $\phi$ and dried.

Using this catalyst, an oxidative dehydrogenation reaction of butene-1 was carried out under condition (3) for activity test.

At a reaction temperature of 370° C., the total conversion of butene-1 was 94% and the yield of butadiene was 82%. When the molar ratio (air/butene-1) of the feed gas was reduced, the oxygen concentration in the outlet gas became nearly zero. Even though the molar ratio (air/butene-1) was returned to the standard condition for activity test, the total conversion of butene-1 fell to 90% and the yield of butadiene fell to 77%.

After the reaction was stopped, the deteriorated catalyst was removed from the reactor after cooling. It was mixed with tellurium-molybdenum containing solid pellets previously prepared (which were prepared by molding a powder as described in Example 12 by the same method as that for the above described catalyst) in an amount of 0.5% based on the catalyst, and the reaction was carried out again.

After carrying out the reaction for 3 hours, the conversion of butene-1 became 80% and the yield of butadiene became 92%.

EXAMPLE 17

A fluidized-bed catalyst having the empirical formula $Fe_{10}Sb_{25}Cu_{0.5}Mo_{0.25}Te_{1.0}O_{68.3}(SiO_2)_{60}$ was used for an ammoxidation reaction of propylene under condition (1) for activity test.

A tellurium-molybdenum enriched catalyst having the same composition as that of the catalyst in this example, except containing 32.9% of tellurium and 7.4% of molybdenum was added to the catalyst during the reaction at 0.9% based on the catalyst.

Although the total conversion of propylene was 98.3% and the yield of acrylonitrile was 78.0% at the beginning, the total conversion of propylene became 99.2% and the yield of acrylonitrile became 78.7% due to the activation processing.

EXAMPLE 18

To a deteriorated catalyst as in Example 13, a tellurium containing solid used in Example 15 (composed of silicon and oxygen in addition to tellurium) was added in an amount of 2% based on the catalyst, and an ammoxidation reaction of propylene was carried out under condition (1) for activity test.

Three hours after the initiation of the reaction, the total conversion of propylene became 96.7% and the yield of acrylonitrile became 84.7%.

COMPARATIVE EXAMPLE 2

To a deteriorated catalyst as in Example 13, a molybdenum containing solid containing 66.7% of molybdenum (composed of oxygen in addition to molybdenum) was added in an amount of 0.15% based on the catalyst, and the reaction was carried out.

The yield of acrylonitrile was 83.3% which was hardly improved, but the total conversion of propylene increased to become 98.1%. As by-products, carbon dioxide slightly increased, and hydrogen cyanide and carbon monoxide increased.

COMPARATIVE EXAMPLE 3

The reaction was carried out using the same method as in Comparative Example 2, except that an amount of the molybdenum containing solid mixed was 0.75% based on the catalyst.

The yield of acrylonitrile decreased to 81.2%. The total conversion of propylene became 99.2%. As by-products, the formation of carbon monoxide and hydrogen cyanide was remarkably increased.

A summary of conditions and results of the above described Examples 12 to 18 and Comparative Examples 2 and 3 are shown in Table 2 below.

TABLE 2

| Composition of Catalyst (atomic ratio) | Condition of Activity Test | Reaction Temperature (°C.) | Contact Time (sec) | Yield of Desired Product (%) | Total Conversion of Organic Compound (%) |
|---|---|---|---|---|---|
| | | | | Yield of Acrylonitrile | Total Conversion of Propylene |
| Example 12 $Fe_{10}Sb_{25}W_{0.25}Te_{1.0}O_{67.8}(SiO_2)_{30}$ | | | | | |
| (A) Before deterioration | (1) | 460 | 6.0 | 80.3 | 98.6 |
| (B) After deterioration | " | " | " | 76.1 | 96.2 |
| (C) After activation processing (Te—Mo—SiO$_2$ containing solid) | " | " | " | 80.5 | 98.0 |
| Example 13 $Fe_{10}Sb_{25}Cu_3Mo_{0.5}W_{0.3}Te_{1.0}O_{73.4}(SiO_2)_{60}$ | | | | | |
| (A) Before deterioration | (1) | 450 | 3.0 | 85.1 | 98.2 |
| (B) After deterioration | " | " | " | 83.0 | 96.5 |
| (C) After activation processing (Te—Mo—SiO$_2$ containing solid) | " | " | " | 85.0 | 98.3 |
| Example 14 As in Example 13 | | | | | |
| (A) Before deterioration | (1) | 450 | 3.0 | 85.1 | 98.2 |
| (B) After deterioration | " | " | " | 83.0 | 96.5 |
| (C) After activation processing (Te—Mo—SiO$_2$ containing solid) | " | " | " | 85.3 | 98.7 |
| | | | | Yield of Hydrogen Cyanide | Total Conversion of Methanol |
| Example 15 $Te_{0.5}Mo_{10}W_1Fe_2Co_3Ni_2Bi_1O_{43.5}(SiO_2)_{50}$ | | | | | |
| (A) Before deterioration | (2) | 430 | 2.0 | 84.1 | 96.2 |
| (B) After deterioration | " | " | " | 82.0 | 94.5 |
| (C) After activation processing (The mixture of Te—Si—O containing solid and Mo containing solid) | " | " | " | 84.3 | 96.5 |
| | | | | Yield of Butadiene | Total Conversion of Butene-1 |
| Example 16 $Fe_{10}Sb_{25}W_{0.25}Te_{1.0}O_{67.8}(SiO_2)_{30}$ | | | | | |
| (A) Before deterioration | (3) | 370 | 6.1 | 82.0 | 94.0 |
| (B) After deterioration | " | " | " | 77.0 | 90.0 |
| (C) After activation processing (Te—Mo—SiO$_2$ containing solid) | " | " | " | 80.0 | 92.0 |
| | | | | Yield of Acrylonitrile | Total Conversion of Propylene |
| Example 17 $Fe_{10}Sb_{25}Cu_{0.5}Mo_{0.25}Te_{1.0}O_{68.3}(SiO_2)_{60}$ | | | | | |
| (A) Before processing | (1) | 460 | 3.5 | 78.0 | 98.3 |
| (C) After activation processing (Te—Mo enriched catalyst) | " | " | " | 78.7 | 99.2 |
| Example 18 As in Example 13 | | | | | |
| (A) Before deterioration | (1) | 450 | 3.0 | 85.1 | 98.2 |
| (B) After deterioration | " | " | " | 83.0 | 96.5 |
| (C) After activation processing (Te containing solid) | " | " | " | 84.7 | 96.7 |
| Comparative Example 2 As in Example 13 | | | | | |
| (A) Before deterioration | (1) | 450 | 3.0 | 85.1 | 98.2 |
| (B) After deterioration | " | " | " | 83.0 | 96.5 |
| (C) After activation processing (Mo containing solid) | " | " | " | 83.3 | 97.3 |
| Comparative Example 3 As in Example 13 | | | | | |
| (A) Before deterioration | (1) | 450 | 3.0 | 85.1 | 98.2 |
| (B) After deterioration | " | " | " | 83.0 | 96.5 |
| (C) After activation processing | " | " | " | 81.2 | 99.2 |

TABLE 2-continued

| Composition of Catalyst (atomic ratio) | Condition of Activity Test | Reaction Temperature (°C.) | Contact Time (sec) | Yield of Desired Product (%) | Total Conversion of Organic Compound (%) |
|---|---|---|---|---|---|
| (Mo containing solid) | | | | | |

EXAMPLES 19-21

A fluidized-bed reactor having an inner diameter of 20 cm (8 inches) was packed with a fluidized-bed catalyst as described in Example 17, and an ammoxidation reaction of propylene was carried out under the following conditions.

| | |
|---|---|
| Apparent Linear Velocity of Feed Gas | 18 cm/sec. |
| Reaction Pressure | 0.5 kg/cm² G |

| Molar Ratio of Feed Gas | |
|---|---|
| O₂ (supplied as the air)/Propylene | 2.2 (molar ratio) |
| NH₃/Propylene | 1.1 (molar ratio) |
| Reaction Temperature | 450° C. |

When the reaction was carried out for 670 hours under the above described conditions, the yield of acrylonitrile decreased and formation of carbon dioxide increased.

This deteriorated catalyst was removed. To every 2 kg of the catalyst, a tellurium-molybdenum containing solid as described in Table 3 below was added, and an ammoxidation reaction of propylene was carried out under condition (1) for activity test.

TABLE 3

| | Composition of Tellurium-Molybdenum Containing Solid (wt %) | | | | | Bulk Density |
|---|---|---|---|---|---|---|
| Example | Te | Mo | Fe | Sb | SiO₂ | (g/ml) |
| 19 | 28.0 | 2.3 | — | — | 61.5 | 0.95 |
| 20 | 31.2 | 7.0 | 2.7 | 6.0 | 39.0 | 1.32 |
| 21 | 9.3 | 2.1 | 5.7 | 31.3 | 37.1 | 0.95 |

The tellurium-molybdenum containing solids in Examples 19 and 20 were those produced by blending starting materials of each component with silica sol, drying by spraying and calcining at 400° C. for 2 hours. The tellurium-molybdenum containing solid in Example 21 was that produced by blending a slurry of iron-antimony oxide previously prepared with molybdenum and tellurium sources and silica sol, drying by spraying and calcining at 400° C. for 2 hours.

The results of activity test are given in the Table 4 below.

TABLE 4

| | Mixing Ratio of Te—Mo Containing Solid to Catalyst % | Activity Test | | | |
|---|---|---|---|---|---|
| | | Conditions | | Results | |
| | | Reaction Temperature (°C.) | Contact Time (sec) | Yield of Acrylonitrile (%) | Conversion of Propylene (%) |
| Catalyst | | | | | |
| Control | | | | | |
| Before deterioration | — | 460 | 3.5 | 78.0 | 98.3 |
| After deterioration | — | 460 | 4.0 | 76.3 | 97.8 |
| Example 19 | 0.9 | 460 | 4.0 | 78.5 | 98.7 |
| Example 20 | 1.0 | 460 | 4.0 | 77.9 | 98.3 |
| Example 21 | 4.5 | 460 | 4.0 | 78.5 | 98.5 |

EXAMPLES 22-28

To every 2 kg of the same deteriorated catalysts as those in Examples 19-21, a tellurium containing solid shown in Table 5 below was added, and an ammoxidation reaction of propylene was carried out under condition (1) described above for activity test.

TABLE 5

| | Composition of Tellurium Containing Solid (wt %) | | | | | | | | | Bulk Density |
|---|---|---|---|---|---|---|---|---|---|---|
| Example | Te | Fe | V | W | Cu | Ti | Zn | Bi | SiO₂ | (g/ml) |
| 22 | 32.0 | — | — | — | — | 12.0 | — | — | 40.0 | 0.81 |
| 23 | 28.0 | — | 1.1 | — | — | — | — | — | 63.0 | 0.92 |
| 24 | 28.0 | — | — | 8.1 | — | — | — | — | 54.8 | 0.98 |
| 25 | 32.0 | 4.2 | — | — | — | — | — | — | 54.0 | 1.13 |
| 26 | 32.0 | — | — | — | 3.2 | — | — | — | 56.0 | 1.11 |
| 27 | 32.0 | — | — | — | — | — | 8.0 | — | 50.0 | 0.96 |
| 28 | 32.0 | — | — | — | — | — | — | 9.0 | 50.0 | 1.18 |

These tellurium containing solids were those prepared by blending the starting materials for each component with silica sol, drying by spraying and calcining at 400° C. for 2 hours.

The results of activity test are shown in Table 6 below.

TABLE 6

| | Mixing Ratio of Te—Mo Containing Solid to Catalyst % | Activity Test | | | |
|---|---|---|---|---|---|
| | | Conditions | | Results | |
| | | Reaction Temperature (°C.) | Contact Time (sec) | Yield of Acrylonitrile (%) | Conversion of Propylene (%) |
| Catalyst | | | | | |
| Control | | | | | |
| Before deterioration | — | 460 | 3.5 | 78.0 | 98.3 |
| After deterioration | — | 460 | 4.0 | 76.3 | 97.8 |
| Example 22 | 1.25 | 460 | 4.0 | 77.6 | 98.1 |
| Example 23 | 1.4 | 460 | 4.0 | 78.0 | 98.5 |
| Example 24 | 1.4 | 460 | 4.0 | 78.1 | 98.5 |

TABLE 6-continued

|  | Mixing Ratio of Te—Mo Containing Solid to Catalyst % | Activity Test | | | |
|---|---|---|---|---|---|
|  |  | Conditions | | Results | |
| Catalyst |  | Reaction Temperature (°C.) | Contact Time (sec) | Yield of Acrylonitrile (%) | Conversion of Propylene (%) |
| Example 25 | 0.5 | 460 | 4.0 | 78.0 | 98.0 |
| Example 26 | 0.9 | 460 | 4.0 | 77.7 | 98.1 |
| Example 27 | 0.9 | 460 | 4.0 | 78.0 | 97.9 |
| Example 28 | 1.0 | 460 | 4.0 | 78.2 | 97.8 |

EXAMPLE 29

A fluidized-bed reactor having an inner diameter of 20 cm (8 inches) was packed with a fluidized-bed catalyst having the empirical formula $Fe_{10}Sb_{25}Cu_{0.5}Mo_{0.2-5}Te_{1.0}O_{68.3}$-$(SiO_2)_{60}$, and an ammoxidation reaction of propylene was carried out under the following conditions.

| Apparent Linear Velocity of Feed Gas | 1.8 cm/sec. |
|---|---|
| Reaction Pressure | 0.5 kg/cm² G |
| Molar Ratio of Feed Gas | |
| O₂ (supplied as the air)/Propylene | 2.2 (molar ratio) |
| NH₃/Propylene | 1.1 (molar ratio) |
| Reaction Temperature | 450° C. |

When the reaction was carried out for 670 hours under the above described conditions, the yield of acrylonitrile decreased and formation of carbon dioxide increased.

This deteriorated catalyst was removed and 2 kg thereof was blended with a tellurium enriched catalyst previously prepared in a dry condition such that the tellurium enriched catalyst is 10% based on the deteriorated catalyst. The reaction was carried out under condition (1) for activity test. The yield of acrylonitrile gradually increased and it became 78.1% after carried out the reaction for 3 hours. When the reaction was carried out using only the deteriorated catalyst under condition (1) for activity test, the yield of acrylonitrile was 76.3%.

The tellurium enriched catalyst used in this example was prepared as follows. 1 kg of a fluidized-bed catalyst having the above described empirical formula (before deterioration) was used. A solution prepared by dissolving 56 g of telluric acid in 0.27 l of water was blended well with the catalyst. After drying at 120° C. for 5 hours, it was calcined at 350° C. for 2 hours. The tellurium content of the resulting tellurium enriched catalyst was 4.4%.

EXAMPLE 30

A fluidized-bed reactor having an inner diameter of 20 cm was packed with a fluidized-bed catalyst having the empirical formula $Fe_{10}Sb_{25}Cu_3Mo_{0.5}W_{0.3}Te_{1.5}O_{73.4}(SiO_2)_{60}$, and an ammoxidation reaction of propylene was carried out under the following conditions.

| Apparent Linear Velocity of Feed Gas | 18 cm/sec |
|---|---|
| Reaction Pressure | 0.5 kg/cm² G |
| Molar Ratio of Feed Gas | |
| Air/Propylene | 10.5 (molar ratio) |
| Ammonia/Propylene | 1.05 (molar ratio) |
| Reaction Temperature | 450° C. |

When the reaction was carried out for 500 hours under the above described conditions, the yield of acrylonitrile deteriorated.

When the deteriorated catalyst was removed and the examination of activity was carried out under condition (1) for activity test, the yield of acrylonitrile was 83%.

This deteriorated catalyst was blended with a previously prepared tellurium-molybdenum enriched catalyst in an amount of 5% based on the deteriorated catalyst in a dry condition, and the reaction was carried out under condition (1) for activity test. The yield of acrylonitrile became 85.3% after 3 hours. The tellurium-molybdenum enriched catalyst used in this example was prepared as follows.

1 kg of the deteriorated catalyst formed was removed. 90 g of a tellurium metal powder was suspended in 220 ml of an aqueous solution of ammonium paramolybdate (containing 10.2 g of the molybdenum component as $MoO_3$), and a 35% hydrogen peroxide solution was added dropwise thereto with heating to prepare a homogeneous solution containing tellurium and molybdenum. To this solution, pure water was added to adjust the liquid quantity to 320 ml. Then, the resulting solution was added to the above described deteriorated catalyst and the mixture was blended well to impregnate the catalyst with the solution. After drying at 120° C. for 16 hours, it was calcined at 450° C. for 2 hours. The resulting tellurium-molybdenum enriched catalyst contained 9.9% of tellurium and 1.1% of molybdenum.

EXAMPLE 31

A deteriorated catalyst as in Example 30 was blended with a previously prepared tellurium-molybdenum enriched catalyst in an amount of 3.5% based on the deteriorated catalyst in a dry condition, and the reaction was carried out under condition (1) for activity test. The yield of acrylonitrile became 85.0% after 4 hours from the initiation of the reaction.

The tellurium-molybdenum enriched catalyst used in this example was prepared as follows.

98 g of a tellurium metal powder was suspended in 240 ml of an aqueous solution of phosphomolybdic acid (containing 33.2 g of the molybdenum component as $MoO_3$), and a 35% hydrogen peroxide solution was added dropwise with heating to prepare a homogeneous solution containing tellurium and molybdenum. To this solution, pure water was added to adjust the liquid quantity to 320 ml. Then, the solution was blended well with the catalyst (before deterioration) in Example 30 to impregnate the catalyst with the solution. After drying at 120° C. for 5 hours, it was calcined at 400° C. for 2 hours. The resulting tellurium-molybdenum enriched catalyst contained 10.3% of tellurium and 2.4% of molybdenum.

A summary of conditions and results of Examples 29 to 31 described above are shown in Table 7 below.

TABLE 7

| Composition of Catalyst (atomic ratio) | Condition of Activity Test | Reaction Temperature (°C.) | Contact Time (sec) | Yield of Acrylonitrile (%) | Total Conversion of Propylene (%) |
|---|---|---|---|---|---|
| Example 29 Fe$_{10}$Sb$_{25}$Cu$_{0.5}$Mo$_{0.25}$Te$_{1.0}$O$_{68.3}$(SiO$_2$)$_{60}$ | | | | | |
| (A) Before deterioration | (1) | 460 | 3.5 | 78.0 | 98.3 |
| (B) After deterioration | " | 460 | 4.0 | 76.3 | 98.0 |
| (C) After activation processing (Te enriched catalyst) | " | 460 | 4.0 | 78.1 | 99.1 |
| Example 30 Fe$_{10}$Sb$_{25}$Cu$_3$Mo$_{0.5}$W$_{0.3}$Te$_{1.5}$O$_{73.4}$(SiO$_2$)$_{60}$ | | | | | |
| (A) Before deterioration | (1) | 450 | 3.0 | 85.1 | 98.2 |
| (B) After deterioration | " | 450 | 3.0 | 83.0 | 96.5 |
| (C) After activation processing (Te—Mo enriched catalyst) | " | 450 | 3.0 | 85.3 | 98.3 |
| Example 31 Fe$_{10}$Sb$_{25}$Cu$_3$Mo$_{0.5}$W$_{0.3}$Te$_{1.5}$O$_{73.4}$(SiO$_2$)$_{60}$ | | | | | |
| (A) Before deterioration | (1) | 450 | 3.0 | 85.1 | 98.2 |
| (B) After deterioration | " | 450 | 3.0 | 83.0 | 96.5 |
| (C) After activation processing (Te—Mo enriched catalyst) | " | 450 | 3.0 | 85.0 | 98.9 |

While the invention has been described in detail and with reference to specific embodiments thereof, it will be apparent to one skilled in the art that various changes and modifications can be made therein without departing from the spirit and scope thereof.

What is claimed is:

1. In the process for the production of nitriles by the ammoxidation reaction of hydrocarbons or alcohols at a temperature of about 300° C. to about 600° C. in a fluidized-bed reactor using a tellurium-containing metal oxide catalyst (A) having a composition, as defined in a freshly prepared state, represented by an empirical formula, $$Sb_{a1}Mo_{a2}V_{a3}Te_bC_cD_dE_eO_x$$

wherein Te represents tellurium, C represents at least one element selected from the group consisting of B, P, As, Bi, S and Se, D represents at least one element selected from the group consisting of Li, Na, K, Rb, Cs and Tl, E represents at least one element selected from the group consisting of Mg, Ca, Sr, Ba, Y, La, Ce, U, Ti, Zr, Nb, Ta, Cr, W, Mn, Re, Fe, Co, Ni, Ru, Rh, Pd, Os, Ir, Pt, Cu, Ag, Zn, Cd, Al, Ga, In, Ge, Sn and Pb, and O represents Oxygen; and a, b, c, d, e and x represent the atomic ratios of the elements in the formula for which they are subscripts, where $a_1+a_2+a_3=10$, $0<a_1+a_2\leq10$ and $0\leq a_3<10$, b=0.01 to 5, c=0 to 10, d=0 to 5, e=0 to 60 and x is the number of oxygen corresponding to the oxides formed by combining the above described components, said catalyst has become partially deactivated during the reaction, the process comprising regenerating the deactivated catalyst at the reaction temperature by contacting the deactivated catalyst with an activity improving agent comprising elemental tellurium while conducting the reaction.

2. A process according to claim 1, wherein the deactivated catalyst (A) is contacted with the activity improving agent in admixture with a second tellurium-containing metal oxide catalyst (B) having the same empirical formula and atomic ratio ranges as catalyst (A), or having the same empirical formula but having one or more atomic ratio ranges different from catalyst (A), or having an empirical formula different from that of catalyst (A).

3. A process according to claim 1, wherein the elemental tellurium is present in an amount of about 0.01 to 30% by weight based on the catalyst (A).

4. A process according to claim 1, wherein the catalyst (A) has a bulk density of about 0.1 to 3 g/ml and a particle size of about 5 to 200 microns.

5. A process according to claim 1, wherein the ratio of the bulk density of the elemental tellurium to the bulk density of the catalyst (A) is in a range of about 0.05:1 to 8:1.

6. A process according to claim 2, wherein the catalyst (B) has a composition represented by the empirical formula of the catalyst (A).

7. A process according to claim 6, wherein the catalyst (B) has the same composition and atomic ratios as the catalyst (A).

8. In the process for the production of nitriles by the ammoxidation reaction of hydrocarbons or alcohols at a temperature of about 300° C. to about 600° C. in a fluidized-bed reaction using a metal oxide catalyst (A) having a composition, as defined in a freshly prepared state, represented by an empirical formula, $$Sb_{a1}Mo_{a2}V_{a3}Te_bC_cD_dE_eO_x$$

wherein Te represents tellurium, C represents at least one element selected from the group consisting of B, P, As, Bi, S and Se, D represents at least one element selected from the group consisting of Li, Na, K, Rb, Cs and Tl, E represents at least one element selected from the group consisting of Mg, Ca, Sr, Ba, Y, La, Ce, U, Ti, Zr, Nb, Ta, Cr, W, Mn, Re, Fe, Co, Ni, Ru, Pd, Os, Ir, Pt, Cu, Ag, Zn, Cd, Al, Ga, In, Ge, Sn and Pb, and O represents oxygen; and a, b, c, d, e and x each represents the atomic ratio of the elements in the formula for which they are subscripts, wherein $a_1+a_2+a_3=10$, $0<a_1+a_2\leq10$ and $0\leq a_3<10$, b=0.01 to 5, c=0 to 10, d=0 to 5, e=0 to 60 and x is the number of oxygen corresponding to the oxides formed by combining the above described components, said catalyst has become partially deactivated during the reaction, the process comprising regenerating the deactivated catalyst at the reaction temperature by contacting the deactivated catalyst with an activity improving agent comprising (1) elemental tellurium and (2) a molybdenum containing material selected from the group consisting of (i) a molybdenum compound not supported on an inert carrier, (ii) a molybdenum enriched metal oxide catalyst having the empirical formula as catalyst (A) above but with a molybdenum content increased by 0.5% by weight or more and (iii) a molybdenum compound supported on an inert carrier, while conducting the reaction.

9. A process according to claim 8, wherein the deactivated catalyst is contacted with the activity improving agent in admixture with a second tellurium-containing metal oxide catalyst (B) having the same empirical formula and atomic ratio ranges as catalyst (A) or having the same empirical formula but having one or more atomic ratio ranges different from catalyst (A), or having an empirical formula different from catalyst (A).

10. A process according to claim 8, wherein the activity improving agent is present in an amount of about 0.01 to 30% by weight based on the catalyst (A).

11. A process according to claim 8, wherein the tellurium content of the activity improving agent is 1% by weight or more.

12. A process according to claim 8, wherein the molybdenum content of the activity improving agent is about 0.5% by weight or more.

13. A process according to claim 8, wherein the atomic ratio of molybdenum:tellurium contained in the activity improving agent is about 0.05:1 to 10:1.

14. A process according to claim 8, wherein the catalyst (A) has a bulk density of about 0.1 to 3 g/ml and a particle size of about 5 to 200 microns.

15. A process according to claim 9, wherein the catalyst (B) has a composition represented by the empirical formula of the catalyst (A).

16. A process according to claim 15, wherein the catalyst (B) has the same composition and atomic ratios as the catalyst (A).

17. A process according to claim 8, wherein the activity improving agent is added to deactivated catalyst (A) such that the increase of tellurium contained in the catalyst-activity improving agent mixture is from about 0.001 to 15% of the total catalyst-activity improving agent mixture weight, and the increase in molybdenum contained in the catalyst-activity improving agent mixture is from about 0.002 to 10% of the total catalyst-activity improving agent mixture weight.

* * * * *